US010472463B2

(12) United States Patent
Hendriks et al.

(10) Patent No.: US 10,472,463 B2
(45) Date of Patent: *Nov. 12, 2019

(54) RESIN, COMPOSITION AND USE

(71) Applicant: DSM IP Assets B.V., Heerlen (NL)

(72) Inventors: Johannes Wilhelmus Maria Hendriks, Echt (NL); Cornelis Eme Koning, Echt (NL); Adrianus Jozephus Hendricus Lansbergen, Echt (NL); Alwin Papegaaij, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 38 days.

This patent is subject to a terminal disclaimer.

(21) Appl. No.: 15/319,135

(22) PCT Filed: Jun. 19, 2015

(86) PCT No.: PCT/EP2015/063865
§ 371 (c)(1),
(2) Date: Dec. 15, 2016

(87) PCT Pub. No.: WO2015/193493
PCT Pub. Date: Dec. 23, 2015

(65) Prior Publication Data
US 2017/0129992 A1 May 11, 2017

(30) Foreign Application Priority Data

Jun. 20, 2014 (EP) .................................... 14173281

(51) Int. Cl.
| C08G 63/553 | (2006.01) |
| C09D 167/08 | (2006.01) |
| C08G 63/78 | (2006.01) |
| C09D 5/02 | (2006.01) |
| C09D 167/00 | (2006.01) |
| C09D 5/03 | (2006.01) |
| C09D 167/06 | (2006.01) |
| C09D 7/20 | (2018.01) |
| C07D 307/00 | (2006.01) |
| C07D 307/34 | (2006.01) |
| C07D 307/46 | (2006.01) |
| C08G 63/48 | (2006.01) |
| C08G 63/181 | (2006.01) |
| C08G 63/16 | (2006.01) |
| C08G 63/127 | (2006.01) |
| C08G 63/64 | (2006.01) |
| C08G 63/18 | (2006.01) |
| C08G 63/52 | (2006.01) |
| C08L 67/08 | (2006.01) |
| C08G 63/02 | (2006.01) |

(Continued)

(52) U.S. Cl.
CPC ........... *C08G 63/553* (2013.01); *C08G 63/78* (2013.01); *C09D 167/08* (2013.01); *C07D 307/00* (2013.01); *C07D 307/34* (2013.01); *C07D 307/46* (2013.01); *C08G 63/02* (2013.01); *C08G 63/12* (2013.01); *C08G 63/123* (2013.01); *C08G 63/127* (2013.01); *C08G 63/16* (2013.01); *C08G 63/18* (2013.01); *C08G 63/181* (2013.01); *C08G 63/20* (2013.01); *C08G 63/21* (2013.01); *C08G 63/48* (2013.01); *C08G 63/52* (2013.01); *C08G 63/64* (2013.01); *C08L 67/06* (2013.01); *C08L 67/08* (2013.01); *C09D 5/02* (2013.01); *C09D 5/022* (2013.01); *C09D 5/03* (2013.01); *C09D 7/20* (2018.01); *C09D 167/00* (2013.01); *C09D 167/06* (2013.01); *Y10T 428/31786* (2015.04); *Y10T 428/31794* (2015.04)

(58) Field of Classification Search
None
See application file for complete search history.

(56) References Cited

U.S. PATENT DOCUMENTS 3,448,066 A * 6/1969 Parker .................. C08G 63/553
428/458
3,457,206 A * 7/1969 Tonner .................. C08G 63/60
525/7

(Continued)

FOREIGN PATENT DOCUMENTS

CN 101679618 3/2010
CN 101679618 A * 3/2010

(Continued)

OTHER PUBLICATIONS

International Search Report for PCT/EP2015/063865, dated Aug. 17, 2015, 3 pages.

(Continued)

*Primary Examiner* — Vivian Chen
(74) *Attorney, Agent, or Firm* — Nixon & Vanderhye P.C.

(57) ABSTRACT

The present invention relates to an alkyd resin comprising the condensation product of at least the following components (A) a polybasic acid, (B) a polyhydric alcohol, and (C) a linear $C_{12}$-$C_{60}$ hydrocarbo monocarboxylic acid, and optionally (D) at least one component other than any of components A to C characterized in that at least a part of the polybasic acid (A) is a (optionally hydrogenated) Diels Alder adduct of citraconic acid with $C_4$-$C_{14}$ conjugated diene, a (optionally hydrogenated) Diels Alder adduct of citraconic anhydride with $C_4$-$C_{14}$ conjugated diene, a half ester of such a Diels Alder adduct and/or a diester of such a Diels Alder adduct.

21 Claims, No Drawings

(51) Int. Cl.
*C08L 67/06* (2006.01)
*C08G 63/12* (2006.01)
*C08G 63/123* (2006.01)
*C08G 63/20* (2006.01)
*C08G 63/21* (2006.01)

(56) References Cited

U.S. PATENT DOCUMENTS

| | | | |
|---|---|---|---|
| 3,745,179 A | 7/1973 | Ibing et al. | |
| 3,920,595 A * | 11/1975 | Anderson | C08G 18/2825 523/400 |
| 4,111,872 A * | 9/1978 | Dworak | C09D 5/4403 204/494 |
| 4,239,672 A * | 12/1980 | Zima | B05D 7/142 427/435 |
| 4,689,266 A | 8/1987 | Eckler | |
| 4,692,483 A * | 9/1987 | Tsuchiya | C09D 151/04 523/201 |
| 4,751,025 A * | 6/1988 | Olechowski | C09F 1/04 530/214 |
| 4,997,480 A * | 3/1991 | Rao | C08G 63/48 106/243 |
| 5,378,757 A * | 1/1995 | Blount, Jr. | C08G 63/48 524/601 |
| 5,959,067 A * | 9/1999 | Bakker | C08G 63/48 428/480 |
| 9,902,870 B2 * | 2/2018 | Hendriks | C09D 167/08 |
| 10,066,053 B2 * | 9/2018 | Koning | C07D 207/404 |
| 10,189,783 B2 * | 1/2019 | Koning | C07D 207/404 |
| 2007/0105976 A1 * | 5/2007 | Nishiguchi | C07C 61/22 523/122 |
| 2008/0020957 A1 * | 1/2008 | Nelson | C08L 93/04 508/449 |
| 2009/0314180 A1 * | 12/2009 | Peterson | C08G 63/48 106/31.6 |
| 2010/0041820 A1 * | 2/2010 | Eslinger | C08G 18/4288 524/539 |
| 2010/0041821 A1 * | 2/2010 | Eslinger | C08L 67/08 524/539 |
| 2012/0214940 A1 * | 8/2012 | Hsu | C08G 61/08 524/604 |
| 2012/0328892 A1 * | 12/2012 | Wu | C08L 61/20 428/524 |
| 2014/0065435 A1 * | 3/2014 | Overbeek | C08F 265/06 428/461 |
| 2014/0256839 A1 * | 9/2014 | Adkins | C08F 8/00 521/163 |
| 2014/0378570 A1 * | 12/2014 | Tabor | C08G 63/553 521/160 |
| 2015/0018563 A1 * | 1/2015 | Tabor | A61Q 5/12 548/478 |
| 2015/0111051 A1 * | 4/2015 | Hendriks | C09D 167/08 428/480 |
| 2016/0237213 A1 * | 8/2016 | Lansbergen | C08G 63/6856 |
| 2017/0327636 A1 * | 11/2017 | Koning | C09D 167/08 |
| 2017/0355672 A1 * | 12/2017 | Koning | C07D 209/48 |
| 2018/0142121 A1 * | 5/2018 | Hendriks | C08G 63/52 |

FOREIGN PATENT DOCUMENTS

| | | | |
|---|---|---|---|
| CN | 102212173 | | 10/2011 |
| CN | 102388080 | | 9/2014 |
| GB | 300130 | | 3/1930 |
| JP | 64-001713 A | * | 1/1989 |
| WO | WO 04/096965 | | 11/2004 |
| WO | WO2008/101722 | | 8/2008 |
| WO | WO 2008/101722 A | * | 8/2008 |
| WO | WO2010/118349 | | 10/2010 |
| WO | 2012/005645 | | 1/2012 |
| WO | WO 2012/158250 A | * | 11/2012 |
| WO | WO 2013/167662 | | 11/2013 |
| WO | WO 2015/052342 | | 4/2015 |

OTHER PUBLICATIONS

Written Opinion of the ISA for PCT/EP2015/063865, dated Aug. 17, 2015, 4 pages.
Official Action, CN Application No. 201580032755.2 (dated May 17, 2018).

* cited by examiner

RESIN, COMPOSITION AND USE

This application is the U.S. national phase of International Application No. PCT/EP2015/063865 filed 19 Jun. 2015, which designated the U.S. and claims priority to EP Patent Application No. 14173281.8 filed 20 Jun. 2014, the entire contents of each of which are hereby incorporated by reference.

The present invention relates to the field of resins for coating compositions in decorative applications such as paints, especially autoxidisable polyester resins such as alkyd resins as well as to methods for making and using such resins and to compositions containing them and for example to prepare dispersions of such resins such as water borne (WB) or solvent borne (SB) emulsions or solutions.

Alkyd paints for professional and do-it-yourself applications are subject to increasing technical and ecological restrictions. Emissions of volatile organic compounds (VOC) must be reduced to protect the environment and the use of high-solid alkyd resins is meant to address this problem. The challenge when formulating high-solids coatings is to lower the resin viscosity without seriously adversely effecting coating properties for example by not increasing drying time and/or increasing yellowing. It is also a preferred object of the invention that the resins have a high biobased content as defined herein. For example it is a more preferred object to reduce or eliminate the use of ingredients such as phthalic anhydride which is not readily available from a biobased source, whilst minimizing any adverse impacts on coating performance.

As used herein unsaturated alkyd resin (for convenience also abbreviated herein to "alkyd resin") denotes a polyester comprising one or more unsaturated fatty acid moieties which is autoxidisable under air at ambient conditions. Alkyd resins and alkyd emulsions are discussed in "Water borne and solvent based alkyds and their end user applications" by N. Tuck, volume VI, Wiley/Sita Series In Surface Coatings technology; (ISBN 471985910) published in 2000.

Current biorenewable alkyd emulsions tend to show undesirable degree of yellowing as well as slow drying. Alkyd resins have a tendency to yellow in the dark. This is even more so for biorenewable alkyd resins containing rosin and relatively much fatty acid. Biorenewable alkyd resins contain or are obtained from biobased building blocks.

Preferred alkyd resins of the invention comprise at least 55%, more preferably at least 65%, most preferably at least 80%, for example at least 95% (e.g. about 100%) by weight of components obtained from a bio-based (i.e. non-fossil, bio-renewable) source. "Bio-renewable components" refer to organic components in which the carbon comes from non-fossil biological sources.

Itaconic/citraconic anhydride and terpene dienes as well as butadiene are mentioned as possible monomers for Diels Alder adducts in an old 1927 IG Farben patent (GB 300130) the authors of whom where Diels and Alder themselves. Preparation and hydrogenation of the adduct of isoprene and citraconic anhydride was discussed in U.S. Pat. No. 3,745,179 assigned to Verba-Chemie AG. A more recent Huntsman patent (WO 2004/096965) describes monoacid functional Diels-Alder adducts of acrylic acid derivatives on myrcene to be used as surfactants. However none of these references suggest using such adducts directly in paints or as polymer precursors to prepare alkyd resins for use in paints.

Renewable alkyd resins have been described in the following documents. The applicant's co-pending application EP13188226.8 filed on 11 Oct. 2013 (now published as WO 2015/052342) describes imide alkyd resins that are prepared from renewable monomers but using a very different chemistry from that described herein. WO2013/167662 (DSM) describes itaconate alkyd resins which may be prepared from biobased sourced raw materials. An itaconate acid or derivative is used as a monomer to prepare a low yellowing alkyd resin.

In contrast the present invention uses itaconic acid and/or itaconic anhydride and/or citraconic anhydride and/or citraconic acid as a raw material for a Diels Alder reaction to prepare acid functional Diels Alder adducts. Such acid functional Diels Alder adducts can be reacted as polymer precursor, either directly in situ or after isolation, in a further polymerisation step to prepare an alkyd resin which itself may optionally also be used to form a coating (e.g. as a paint). Further, WO2013-167662 does not describe the use of Diels Alder adducts as used in the present invention.

Surprisingly the applicant has found that certain citraconic acid or citraconic acid anhydride based Diels Alder adducts can be used as monomers in synthesis of alkyd resins. The adducts are prepared from (i) citraconic acid and/or citraconic acid anhydride and/or itaconic acid and/or itaconic anhydride and (ii) a $C_4$-$C_{14}$ conjugated diene, such as for example butadiene, isoprene (yielding dimethyl tetrahydrophthalic anhydride or DMTHPA), or $C_4$-$C_{14}$ conjugated diene functional terpenes such as myrcene, phellandrene and α-terpinene. The Diels Alder adduct that is present in the condensation product of the alkyd resin of the present invention can also be prepared from itaconic acid and/or itaconic anhydride, in which case isomerization of itaconic acid/itaconic anhydride has to take place during preparation of the Diels Alder adduct, which can be effected by preparing the Diels Alder adduct at increased temperature, for example at a temperature higher than 50° C. The $C_4$-$C_{14}$ conjugated diene, can also be prepared in situ from a diene in the presence of a suitable isomerization catalyst such as iodine or a strong acid like phosphoric acid. This in situ preparation is in particular suitable for the preparation of $C_4$-$C_{14}$ conjugated diene functional terpenes, such as for example the preparation of $C_4$-$C_{14}$ conjugated diene functional terpene from limonene. The $C_4$-$C_{14}$ conjugated diene used in the present invention to prepare the Diels Alder adduct is preferably a $C_4$-$C_{14}$ conjugated diene that does not contain carboxylic acid functionality. The adducts can be hydrogenated if preferred, but this is not necessary. Structures of some examplary adducts are shown below.

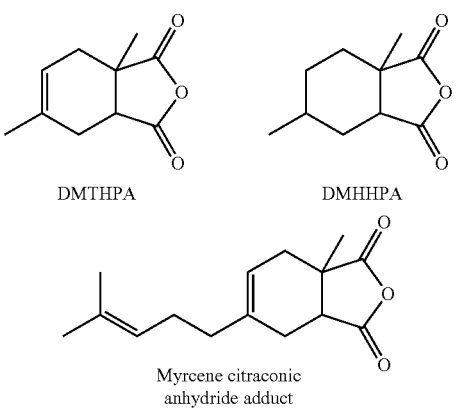

DMTHPA    DMHHPA

Myrcene citraconic
anhydride adduct

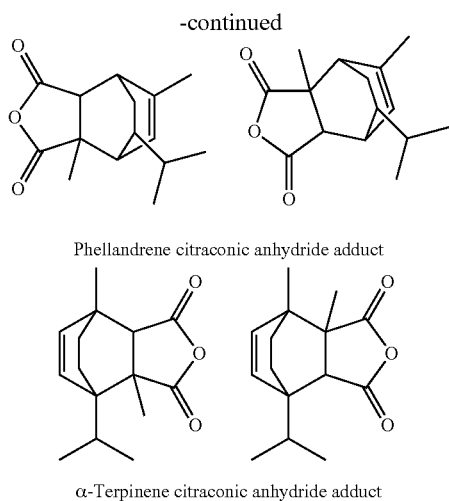

Phellandrene citraconic anhydride adduct

α-Terpinene citraconic anhydride adduct

Preferably, citraconic acid and/or citraconic anhydride are used to prepare the Diels Alder adducts. More preferably, citraconic anhydride is used to prepare the Diels Alder adducts used to prepare the alkyd resins of the present invention.

Unexpectedly it has been discovered that such adducts can replace phthalic acid and/or phthalic anhydride (in whole or in part) as a monomer for preparing alkyd resins for use in paints. Alkyd resins prepared with such adducts surprisingly show improved or comparable properties when used in paints, such as good drying, high hardness and/or even more surprisingly low yellowing. This high hardness is in particular remarkably for cycloaliphatic monomers based on the Diels Alder adducts as used in the present invention replacing aromatic monomers.

Therefore in accordance with the present invention there is provided an alkyd resin comprising the condensation product of at least the following components
  (A) a polybasic acid (and/or a derivative of a polybasic acid such as an ester and/or an anhydride of a polybasic acid),
  (B) a polyhydric alcohol, and
  (C) a linear $C_{12}$-$C_{60}$ hydrocarbo carboxylic acid, and
optionally (D) at least one component other than any of components (A) to (C) wherein at least a part of the polybasic acid (A) is a (optionally hydrogenated) Diels Alder adduct of citraconic acid with $C_4$-$C_{14}$ conjugated diene, a (optionally hydrogenated) Diels Alder adduct of citraconic anhydride with $C_4$-$C_{14}$ conjugated diene, a half ester of such a Diels Alder adduct and/or a diester of such a Diels Alder adduct.

Broadly in a further aspect of the invention there is provided a process for preparing an unsaturated alkyd resin comprising the steps of
  a. preparing (optionally hydrogenated) Diels Alder adduct of citraconic acid with $C_4$-$C_{14}$ conjugated diene and/or a (optionally hydrogenated) Diels Alder adduct of citraconic anhydride with $C_4$-$C_{14}$ conjugated diene, and
  b. reacting the Diels Alder adduct obtained in a) directly after preparation or alternatively after collection and isolation in an esterification step with an alkyd prepolymer to form the alkyd resin.
Broadly in a further aspect of the invention there is provided a process for preparing an unsaturated alkyd resin comprising the steps of
  a. preparing (optionally hydrogenated) Diels Alder adduct of citraconic acid with $C_4$-$C_{14}$ conjugated diene, a (optionally hydrogenated) Diels Alder adduct of citraconic anhydride with $C_4$-$C_{14}$ conjugated diene and/or a diester of such a Diels Alder adduct, and
  b. reacting, in an (trans)esterification step, the Diels Alder adduct obtained in a) directly after preparation or alternatively after collection and isolation with components B, C and D and optionally with additional polybasic acid (A) to form the alkyd resin.

In another aspect, the invention provides an alkyd resin obtained and/or obtainable by either process of the invention.

A yet other aspect of the present invention provides a coating composition comprising an alkyd resin of the invention. Preferred coating compositions of the invention are selected from the group consisting of: a solvent based paint and a water based paint.

A still other aspect of the invention provides a substrate or article coated with a coating composition of the invention.

A yet still other aspect of the invention provides a method of coating a substrate or article comprising the steps of
  A) coating the substrate or article with a coating composition of the invention; and.
  B) optionally drying the composition in situ and/or optionally curing the composition in situ to form a cured coating thereon.

Alkyd resins prepared from the Diels Alder based building blocks of the invention can be prepared without using ingredients such as rosins and thus increasing the drying rate. Preferably, the alkyd resins are prepared without using rosins. These Diels-Alder adducts can be used as building blocks that replace (or whole or in part) non-renewable aromatic acid monomers, such as phthalic acid and/or phthalic anhydride, and yet provide the same level of hardness. Faster drying and/or higher hardness and/or better yellowing can be achieved with respect to prior art renewable alkyd resins.

The Diels Alder adducts used in the present invention are prepared from (i) citraconic acid and/or citraconic acid anhydride and/or itaconic acid and/or itaconic anhydride and (ii) a $C_4$-$C_{14}$ conjugated diene. The citraconic acid and citraconic anhydride preferably used to prepare the adduct in the present invention may be prepared from itaconic acid/ itaconic acid anhydride, as such the alkyd resin of the present invention may contain, next to citraconic acid/ citraconic anhydride adduct, also Diels Alder adduct of itaconic acid/anhydride with the $C_4$-$C_{14}$ conjugated diene.

Preferably, the $C_4$-$C_{14}$ conjugated diene is selected from the group consisting of 1,3-butadiene, isoprene, terpene(s) containing conjugated double bonds and any mixture thereof. A preferred terpene already containing conjugated double bonds is myrcene. In another preferred embodiment, the terpene containing conjugated double bonds is prepared in situ by treating a terpene such as limonene with an isomerization catalyst such as a strong acid, for example phosphoric acid. Most preferably, the Diels Alder adducts present in the alkyd resin of the present invention are prepared from isoprene, myrcene, phellandrene, limonene treated with isomerization catalyst or from a mixture of at least two of these dienes.

Preferably, in the alkyd resin according to the present invention, at least a part of the polybasic acid (A) is a (optionally hydrogenated) Diels Alder adduct of citraconic anhydride with $C_4$-$C_{14}$ conjugated diene.

Citraconic anhydride can be obtained fully from biobased materials. For example citraconic anhydride can be made from biobased itaconic acid, if necessary in-situ. Preferably, the diene, used to prepare the reaction product with citraconic acid and/or citraconic acid anhydride, is also obtained from a biobased source. For example, isoprene and others like limonene will be available in biobased grade in the near future, and myrcene is a natural product. The double bond in the Diels Alder adduct can be used as such, giving improved hardness in alkyd resins (probably by extra oxidation reactions) or can be hydrogenated, to give an aliphatic material with even further reduced yellowing.

"Terpene" refers to the naturally occurring oligomers of isoprene and their derivatives, or their synthetic counterparts, e.g. from pyrolysis of waste streams. A terpene contains two or more isoprene residues. Certain terpenes are known to possess conjugated double bonds, and therefore to be capable of undergoing Diels Alder addition reactions with dienophiles. Others do not contain conjugated double bonds but can be isomerized to give conjugated double bonds (such as for example limonene). The terpene is preferably a mono-, sesque-, or diterpene, and is desirably a hydrocarbon. A preferred terpene for use as the diene is myrcene and/or limonene.

Terpenes can be used for Diels-Alder reactions with maleic- and citraconic anhydride. The use with maleic anhydride is one of the classic Diels-Alder reactions and described many times. The use of citraconic anhydride is new and no precedents are known. Conjugated terpenes like alpha-terpinene and alpha-phellandrene can be reacted at 170° C. for a few hours with citraconic anhydride to obtain the expected Diels-Alder adducts. Non-conjugated terpenes like limonene also can be used for Diels-Alder reactions by adding an isomerization agent like phosphoric acid to the reaction mixture with citraconic anhydride, giving the same products as the above mentioned alpha-terpenes. The present invention therefore also relates to Diels Alder adducts obtained from citraconic acid or citraconic anhydride with conjugated terpenes such as alpha-terpinene and alpha-phellandrene and also Diels Alder adducts obtained from citraconic acid or citraconic anhydride with conjugated terpenes obtained by treating terpenes, such as for example limonene, with an isomerization catalyst.

The preparation of the adduct used in the present invention may be carried out in the conventional manner for Diels Alder additions by heating the reaction mixture of the monomers, in substantially stoichiometric proportions or with excess of diene and optionally in a suitable organic solvent, if required for fluidity. A Diels Alder catalyst, e.g. a Lewis acid such as aluminium chloride may be employed, however un-catalysed reactions are preferred. The reaction temperature is preferably greater than 50° C., more preferably greater than 70° C. and preferably lower than the decomposition temperature of the product. The elevated temperature is maintained for a sufficient time to obtain an acceptable yield of the adduct. The time required depends on the reactivity of the particular reagents, the temperature, the stability of the product and commercial considerations (e.g. the value of the product against the cost of prolonging the heating step), however, typically, it is greater than 30 minutes, preferably greater than one hour, more preferably greater than two hours. The preparation of the adduct used in the present invention can be effected with pressure as well as without pressure, but is preferably effected with pressure as lower temperatures are possible for obtaining the same conversions as without pressure. The preparation of the adduct based on volatile reactant is preferably effected with pressure. The preparation of the adduct used in the present invention is preferably effected in the presence of a polymerization inhibitor, for example hydroquinone.

Preferably, the total amount of the Diels Alder adducts as specified above [i.e. (optionally hydrogenated) Diels Alder adduct of citraconic acid with $C_4$-$C_{14}$ conjugated diene, a (optionally hydrogenated) Diels Alder adduct of citraconic anhydride with $C_4$-$C_{14}$ conjugated diene, a half ester of such a Diels Alder adduct and/or a diester of such a Diels Alder adduct] present in the alkyd resin is at least 25 wt. %, more preferably at least 50 wt. % (relative to the total weight amount of polybasic acid present in the alkyd resin), more preferably at least 75 wt. %, even more preferably the amount of the Diels Alder adducts as specified above present in the alkyd resin is 100 wt. % (relative to the total weight amount of polybasic acid present in the alkyd resin).

Preferably, the amount of components (A), (B), (C) and (D) used to prepare the alkyd resin of the present invention is from 10 to 50% by weight of (A), more preferably from 15 to 40% by weight of (A); from 10 to 40% by weight of (B)), more preferably from 15 to 30% by weight of (B); from 1 to 80% by weight of (C), more preferably from 10 to 70 wt. %, even more preferably from 20 to 70% by weight of (C), whereby the amount of the total of Components (A) to (D) being 100 wt. %.

The alkyd resin according to the present invention preferably comprises the condensation product of components (A), (B), (C) and (D).

Component (A) of the alkyd resin of the present invention is a polybasic acid and/or a derivative of a polybasic acid such as an ester and/or an anhydride of a polybasic acid. In case the alkyd resin of the present invention includes another polybasic acid than the Diels Alder adducts as specified above, the additional polybasic acid is preferably selected from phthalic acid, maleic acid, fumaric acid, azelaic acid, succinic acid, itaconic acid, adipic acid, sebacic acid, furandicarboxylic acid, trimellitic acid, pyromellitic acid and any mixture thereof. Also here a derivative of the polybasic acid such as an ester and/or anhydride of the mentioned polybasic acid can be used. However, the amount of phthalic acid monomer (introduced by the use of phthalic acid and/or phthalic anhydride) in the alkyd resin is preferably lower than 25 wt. % (relative to the total weight amount of alkyd resin), more preferably lower than 20 wt. %, even more preferably lower than 15 wt. %, even more preferably lower than 10 wt. %, even more preferably lower than 5 wt. %, most preferably at most 2 wt. % and most preferably 0 wt. %. Preferably, the total amount of Diels Alder adduct of conjugated diene and maleic acid and Diels Alder adduct of conjugated diene and maleic acid anhydride present in the alkyd resin of the present invention is lower than 15 wt. % (relative to the total weight amount of alkyd resin), preferably lower than 10 wt. %, even more preferably lower than 5 wt. %, most preferably at most 2 wt. % and most preferably 0 wt. %.

Component (B) of the alkyd resin of the present invention is a polyalcohol, preferably a polyalcohol with at least three hydroxyl groups; preferably selected from glycerol; trimethylolpropane, pentaerythritol; mannitol, sorbitol, sorbitan and any mixture thereof; more preferably selected from glycerol, pentaerythritol and a mixture thereof.

Component (C) of the alkyd resin of the present invention is preferably a fatty acid or a mixture of fatty acids. The fatty acid preferably comprises at least one, preferably at least two double bonds, more preferably at least two non-conjugated double bounds preferably selected from a linoleically unsaturated moiety (=linoleic unsaturation). Preferably, the fatty acids are obtained from natural sources such as soyabean fatty acid, sunflower fatty acid, tall oil fatty acid, linseed oil fatty acid, preferably soyabean fatty acid, sunflower fatty acid, tall oil fatty acid.

Component (D) that is optionally present in the alkyd resin of the present invention is for example benzoic acid, sulfonated benzoic acid, sulfonated isophthalic, dimethylolpropionic acid or neutralized derivative of sulfonated itaconic acid, sulfonated benzoic acid, sulfonated isophthalic, dimethylolpropionic acid, polyisocyanate (mostly diisocyanate).

The present invention further relates to an alkyd resin as described above which is solvent borne or a solid. In one embodiment, the alkyd resin is a solid, whereby the alkyd resin is the condensation product as described above. In another embodiment, the alkyd resin comprises the condensation product as described above in an amount of preferably at least 50 wt. % (relative to the alkyd resin) and further comprises solvent and/or diluent.

The present invention further also relates to a water borne alkyd emulsion comprising the condensation product as described above and water, and where optionally at least one surfactant (preferably a mixture of nonionic and ionic surfactants) is added after the reaction of Components A to D and where optionally at least one surfactant (preferably a mixture of nonionic and ionic surfactants) is added during the reaction of components A to D. Suitable surfactants include but are not limited to conventional anionic, cationic and/or nonionic surfactants such as Na, K and $NH_4$ salts of dialkylsulphosuccinates, Na, K and $NH_4$ salts of sulphonated oils, Na, K and $NH_4$ salts of alkyl sulphonic acids, Na, K and $NH_4$ salts of alkyl sulphates, alkali metal salts of sulphonic acids; fatty alcohols, ethoxylated fatty acids and/or fatty amides, and Na, K and $NH_4$ salts of fatty acids such as Na stearate and Na oleate. Other anionic surfactants include alkyl or (alk)aryl groups linked to sulphonic acid groups, sulphuric acid half ester groups (linked in turn to polyglycol ether groups), phosphonic acid groups, phosphoric acid analogues and phosphates or carboxylic acid groups. Cationic surfactants include alkyl or (alk)aryl groups linked to quaternary ammonium salt groups. Non-ionic surfactants include polyglycol ether compounds and polyethylene oxide compounds. The surfactants may also be polymeric surfactants which are also described as wetting agents. The amount of total surfactants used is preferably at least 0.1%, more preferably at least 1% by weight, most preferably at least 3% by weight and preferably less than 11%, more preferably less than 9% and most preferably less than 7% by weight based on the weight of the total resin material. Preferably a mixture of anionic and non-ionic surfactants are used.

The present invention also relates to a coating composition comprising an alkyd resin as described above and/or an alkyd resin obtained by the process as described above. In a preferred embodiment, the coating composition is water borne. In another embodiment, the coating composition is solvent borne. The present invention also relates to a substrate or article having coated thereon an (optionally cured) coating composition as described herein.

The present invention also relates to a method of using an alkyd resin as described above and/or an alkyd resin obtained by the process as described above to prepare a coating composition as described above. The present invention also relates to a method for preparing a coated substrate or article comprising the steps of applying a coating composition as described herein to a substrate or article; optionally drying the composition in situ and/or optionally curing the composition in situ to form a coating thereon.

The invention is now demonstrated by means of a series of examples and comparative examples. All examples are supportive of the scope of claims. The invention, however, is not restricted to the specific embodiments as shown in the examples.

Test Methods

Acid Number

The acid number (or AN) is given as the mass of potassium hydroxide (KOH) in milligrams that is required to neutralize one gram of the tested substance and is used as a measure of the concentration of carboxylic acid groups present. AN is determined conventionally by titration and/or using ASTM D974.

Gloss Measurement Method

Gloss measurements were carried out on a BYK Gardner micro TRI gloss 20 60 85 glossmeter in accordance with ASTM D523 89.

König Hardness

König hardness was determined following DIN 53157 NEN 5319 using an Erichsen hardness equipment. The values are given in seconds (s). Preferably the unpigmented composition of the invention has a König hardness of at least 30 seconds after 4 weeks.

Molecular Weight Determination (Weight Average Mw)

Unless the context dictates otherwise, the molecular weights referred to in this application are weight average molecular weight (also denoted herein as Mw) as determined on an Alliance Waters 2695 GPC with two consecutive PL-gel columns, type Mixed-C, I/d=300/7.5 mm (Polymer Laboratories), size of column particles 10 μm, using stabilised tetrahydrofuran (THF) modified with 0.8% acetic acid as the eluent at 1 mL/min at 40° C. and using an Alliance Waters 2414 refractive index detector at 40° C. A set of polystyrene standards with a molecular weight range of from 500 to $7 \times 10^6$ g/mol was used to calibrate the GPC equipment.

Molecular Weight Calculation (Number Average Mn)

Unless the context dictates otherwise where a number average molecular weight (also denoted herein as Mn) is mentioned this is measured using the same apparatus in the manner described above.

Standard Conditions

As used herein, unless the context indicates otherwise, standard conditions (e.g. for drying a film) means a relative humidity of 50%±5%, ambient temperature (23° C.±2°) and an air flow of less than or equal to 0.1 m/s.

Drying Properties (Cotton Wool Dust Free Time (DFT) and Tack Free Time (TFT) Tests)

A cotton wool adhesion test measures the rate of surface drying of a coating film. The cotton wool adhesion test was conducted on a coating film applied with a 100 μm slit applicator on a glass plate. After applying the coating composition, a swatch of cotton wool (a loose ball of approximately 0.2 g and a diameter of approximately 3 cm) was dropped from a height of 5 cm on the paint film. After 10 seconds the glass panel was turned over 180° and it was observed if the cotton wool dropped off without leaving cotton fibres on the surface. When the cotton wool did not stick to the surface, the time was recorded as the dust free time. For the tack free time the same procedure was used, but now a weight of 1 kg was placed on the cotton wool. The tack free time was always determined after dust-free properties were reached.

Yellowing

Colour change due to yellowing is measured according to CieLab. A coating film is applied with a 100 μm slit applicator on a glass plate and dried for one week at room temperature. Then initial colour according to CieLab (L-value, a-value, b-value) is measured and b-value recorded. Next the film is stored in an oven at 50° C. for 2 week. Again colour is measured and change in b-value is recorded as Δb. The higher Δb, the stronger the yellowing is. Reliability is improved by further measurements after 3 weeks.

EXAMPLES AND COMPARATIVE EXPERIMENTS

Example 1a

DMTHPA

The adduct of isoprene and citraconic anhydride was prepared by mixing the monomers (isoprene in 5% excess) with 250 ppm hydroquinone in a stirred pressure reactor and heating to 85° C. for 12 hours. After a distillation step about 92% product was isolated as a mobile liquid and identified as a mixture of 2 isomers of dimethyl tetrahydrophthalic anhydride (DMTHPA) by H NMR. Purity was estimated 99.8% by GC.

Example 1b

Alkyd Resin from DMTHPA

An alkyd resin was prepared by reacting 35.0 grams of DMTHPA prepared according to example 1a, 26.6 grams of pentaerythritol, 16.5 grams of benzoic acid and 37.1 grams of soyabean fatty acids at max 230° C. Esterification was conducted using azeotropic water removal until acid value below 15 mgKOH/g. The resin was cooled down, diluted in xylene and poured out. Resin properties are shown in table 1.

Comparative Examples Comp A to C

A comparative alkyd resin A was prepared by reacting 168.2 grams of phthalic anhydride (PA), 155.4 grams of pentaerythritol, 96.2 grams of benzoic acid and 217 grams of soyabean fatty acids at max 230° C. Esterification was conducted by azeotropic water removal until acid value below 15 mgKOH/g. The resin was cooled down, diluted in xylene and poured out.

Comparative resins B and C respectively were produced by replacing phthalic anhydride on a molar basis in the method described in comparative example A above with respectively tetrahydro phthalic anhydride (THPA) or Methyl tetrahydrophthalic anhydride (MTHPA). MTHPA is produced by Polynt SpA. Resin properties are shown in table 1.

Example 2a

DMHHPA

DMTHPA prepared according to example 1a was hydrogenated using a supported palladium catalyst in a stirred pressure reactor to yield dimethylhexahydro phthalic anhydride (DMHHPA). H NMR showed conversion of the C=C double bond, GC showed presence of 4 compounds being formed and mass spectrometry (using chemical ionization) showed that the MW of all 4 peaks is 182 (MW of Diels-Alder adduct starting material is 180). Further fragmentation pattern of all 4 peaks (using electron impact) indicated they are all isomers/diastereomers.

Example 2b

Alkyd Resin from DMHHPA

An alkyd resin was prepared by reacting 45.6 grams of DMHHPA prepared according to example 2a, 34 grams of pentaerythritol, 21.1 grams of benzoic acid and 47.5 grams of soyabean fatty acids at max 230° C. Esterification was conducted using azeotropic water removal until acid value below 15 mgKOH/g. The resin was cooled down, diluted in xylene and poured out. Resin properties are shown in table 1.

Comparative Examples Comp D and E

Comparative resins D and E respectively were produced by replacing phthalic anhydride on a molar basis in the method described in comparative example A above with respectively hexahydro phthalic anhydride (HHPA) or Methyl hexahydrophthalic anhydride (MHHPA). MHHPA is produced by Polynt SpA. Resin properties are shown in table 1.

Example 3a

Citraconic Anhydride—Myrcene Adduct

The adduct of myrcene and citraconic anhydride was prepared by mixing the monomers in equivalent amounts at room temperature in a stirred reactor and heating to 180° C. for 2 hours. After a distillation step about 97% product was isolated as a slightly yellow mobile liquid of which identity was confirmed by H NMR.

Example 3b

Alkyd Resin from Citraconic Anhydride—Myrcene Adduct

An alkyd resin was prepared by reacting 234 grams of adduct prepared according to example 3a, 137.7 grams of pentaerythritol, 80.1 grams of benzoic acid and 230.6 grams of soyabean fatty acids at max 240° C. Esterification was conducted using azeotropic water removal until acid value below 15 mgKOH/g. The resin was cooled down, diluted in xylene and poured out. Resin properties are shown in table 1.

Example 4a

Alkyd Resin from DMTHPA Adduct

An alkyd resin was prepared by reacting 227.4 grams of adduct prepared according to example 1a, 170.5 grams of pentaerythritol, 105.6 grams of benzoic acid and 238.2 grams of soyabean fatty acids at max 240° C. Esterification was conducted using azeotropic water removal until acid value below 12 mgKOH/g. The resin was cooled down, and it was diluted with xylene. The resin was poured out.

Example 5a

Alkyd Resin from DMHHPA

An alkyd resin was prepared by reacting 513 grams of adduct prepared according to example 2a, 361 grams of pentaerythritol, 178 grams of benzoic acid and 532 grams of soyabean fatty acids at max 250° C. Esterification was conducted using azeotropic water removal until acid value below 12 mgKOH/g. The resin was cooled down, and xylene was removed by vacuum distillation. The resin was poured out and used in example 5b.

Example 5b

Emulsion Resin from DMHHPA 302 grams of the solid resin from example 6a were emulsified as follows. The resin was heated to between 50-80° C. and 51 grams of a 30% solution of a highly branched alcohol based surfactant combining anionic and non-ionic components and 14 grams of demineralised water were added. The mixture was neutralised with a non-amine base and was stirred until homogeneous. Demineralised water was added during 2 hours until a solids content of 53% was obtained. The emulsion showed a milky appearance and was stable.

Example 6a

Alkyd Resin from Citraconic Anhydride—Myrcene Adduct

An alkyd resin was prepared by reacting 351 grams of adduct prepared according to example 3a, 200 grams of pentaerythritol, 116 grams of benzoic acid and 335 grams of soyabean fatty acids at max 240° C. Esterification was conducted using azeotropic water removal until acid value below 12 mgKOH/g. The resin was cooled down, and xylene was removed by vacuum distillation. The resin was poured out and used in example 6b.

Example 6b

Emulsion Resin from Citraconic Anhydride—Myrcene Adduct 348 grams of the solid resin from example 6a were emulsified as follows. The resin was heated to between 50-80° C. and 59 grams of a 30% solution of a highly branched alcohol based surfactant combining anionic and non-ionic components and 25 grams of demineralised water were added. The mixture was neutralised with a non-amine base and was stirred until homogeneous. Demineralised water was added during 2 hours until a solids content of 51% was obtained. The emulsion showed a milky appearance and was stable.

Comparative examples Comp F and G

A comparative adduct F was prepared using maleic anhydride and myrcene with the process of example 3a.

A comparative alkyd resin G was prepared by replacing Citraconic anhydride—myrcene adduct on a molar basis in the method described in example 3b above with Maleic anhydride—myrcene adduct F. Resin properties are shown in table 1.

Comparative Example Comp H

A resin containing rosin—citraconic anhydride adduct as exemplified in WO2013/167662 was prepared as follows: 400 g of tall oil fatty acids, 450 g of tall rosin and 114 g of itaconic acid were charged to a reactor fitted with thermocouple, stirrer, nitrogen flow and Dean-Stark trap, and heated to 180° C. After 2 hours the reactor was cooled to 120° C. and 175 g of glycerol were charged to the reactor. The reactor was heated to 250° C. under xylene reflux conditions and the distillation was stopped when the acid value reached 10 mg KOH/g resin. The reactor was then cooled to 180° C. and vacuum distillation was started for removal of xylene azeotropic solvent. After cooling down to below 100° C. the resin was poured out. Resin properties are shown in table 1.

Comparative Example Comp J

A resin containing rosin—citraconic anhydride adduct as exemplified in WO2013/167662 was prepared as follows: 536 g of tall oil fatty acids, 203 g of tall rosin and 183 g of itaconic acid were charged to a reactor fitted with thermocouple, stirrer, nitrogen flow and Dean-Stark trap, and heated to 180° C. After 2 hours the reactor was cooled to 120° C. and 184 g of glycerol were charged to the reactor. The reactor was heated to 250° C. under xylene reflux conditions and the distillation was stopped when the acid value reached 15 mg KOH/g resin. The reactor was then cooled to 180° C. and vacuum distillation was started for removal of xylene azeotropic solvent. After cooling down to below 100° C. the resin was poured out. Resin properties are shown in table 1.

Comparative Example Comp K

Emulsion Resin

Comparative emulsion K was prepared as follows: A sample of comparative alkyd resin Comp A was freed of xylene by distillation and used in the preparation procedure exemplified in Example 6b. The resulting emulsion had a solids content of 53%, showed a milky appearance and was stable.

TABLE 1

Resin characteristics

| Example | Resin based on: | Acid value mgKOH/g | Mn Da | Mw kDa |
|---|---|---|---|---|
| 1b | DMTHPA | 6 | 2760 | 12 |
| 2b | DMHHPA | 14 | 2310 | 9 |
| 3b | Myrcene—citraconic anhydride adduct | 10 | 2960 | 20 |
| 4a | DMTHPA | 10 | 2980 | 36 |
| 5a | DMHHPA | 11 | 3700 | 40 |
| 6a | Myrcene—citraconic anhydride adduct, oil length 40% | 9 | 2960 | 16 |
| Comp A | PA | 15 | 3050 | 19 |
| Comp B | THPA | 11 | 3810 | 189 |
| Comp C | MTHPA | 14 | 3150 | 40 |
| Comp D | HHPA | 14 | 3140 | 26 |
| Comp E | MHHPA | 13 | 3130 | 21 |
| Comp G | Myrcene—maleic anhydride adduct | 12 | 3420 | 85 |
| Comp H | Rosin—citraconic anhydride adduct, oil length 40% | 8 | 1760 | 26 |
| Comp J | Rosin—citraconic anhydride adduct, oil length 66% | 16 | 1970 | 105 |

Example 7

Paints

Paints were produced by mixing in a Cowless dissolver resin solution (44 grams solid resin), 28 grams of Tioxide TR 92 (pigment) and 0.30 grams of Nuosperse FA 601 (dispersant) and milling them into a mill paste. To this paste were added under stirring 0.31 grams Borchi-Oxy-Coat (iron drier), 0.70 grams Calcium naphthenate (calcium drier), 1.83 grams Octasoligen Zirconium 12 (zirconium drier), 0.3 grams Borchinox M2 (antiskinning agent) and xylene to give application viscosity.

These paints showed the following properties (table 2).

| Paint | Paint A1 | Paint B1 | Paint C1 | Ex 7 |
|---|---|---|---|---|
| Example resin used in paint | Comp A | Comp B | Comp C | Ex 1b |
| Resin based on: | PA | THPA | MTHPA | DMTHPA |
| Cotton wool drying, 100 μm wet | | | | |
| dust free time (hr:min) | 0.25 | 0.47 | 1.02 | 1.01 |
| tack free time (hr:min) | 2.25 | 2.17 | 4.02 | 4.01 |
| König Hardness in sec, 100 μm wet | | | | |
| 1 day | 31 | 19 | 19 | 20 |
| 7 days | 49 | 34 | 28 | 48 |
| 14 days | 66 | 40 | 40 | 63 |
| 28 days | 77 | 45 | 59 | 87 |
| Yellowing in the dark, 100 μm wet | | | | |
| b* Initial | 2.11 | 2.21 | 2.47 | 2.42 |
| db* after 14 days 50° C. | 1.32 | 2.05 | 1.43 | 0.78 |
| db* after 21 days 50° C. | 1.87 | 3.16 | 2.04 | 1.13 |

The results show that the paint (Example 7) formulated with a resin of the invention (Example 1b prepared from DMTHPA monomer (adduct of myrcene and citraconic anhydride) according to the invention—Example 1a) shows better final hardness and yellowing results in comparison with prior art Paints A1, B1 and C1 respectively formulated from comparative resins Comp A, B and C. Interestingly Example 7 is a better paint than Paint A1 prepared using a resin (Comp A) made from a phtalic anhydride PA monomer, having much better yellowing and comparable hardness development and even better final hardness. Furthermore it is particularly surprising that Example 7 also has much better properties than Paints B1 and C1 formulated from resins prepared from monomers of respectively THPA (Comp B) and MTHPA (Comp C), which are maleic anhydride based analogues of DMTHPA.

Example 8

Paints

Paints were produced by mixing in a Cowless dissolver resin solution (44 grams solid resin), 28 grams of Tioxide TR 92 (pigment) and 0.30 grams of Nuosperse FA 601 (dispersant) and milling them into a mill paste. To this paste were added under stirring 0.31 grams Borchi-Oxy-Coat (iron drier), 0.70 grams Calcium naphthenate (calcium drier), 1.83 grams Octasoligen Zirconium 12 (zirconium drier), 0.3 grams Borchinox M2 (antiskinning agent) and xylene to give application viscosity.

These paints showed the following properties (table 3).

| Paint | Paint A2 | Paint D1 | Paint E1 | Ex 8 |
|---|---|---|---|---|
| Example resin used in paint | Comp A | Comp D | Comp E | Ex 2b |
| Resin based on: | PA | HHPA | MHHPA | DMHHPA |
| Cotton wool drying, 100 μm wet | | | | |
| dust free time (hr:min) | 0:19 | 0:43 | 0:31 | 1:40 |
| tack free time (hr:min) | 4:57 | 5:21 | 5:04 | 5:19 |
| König Hardness in sec, 100 μm wet | | | | |
| 1 day | 33 | 19 | 23 | 24 |
| 7 days | 49 | 28 | 34 | 40 |
| 14 days | 63 | 40 | 49 | 54 |
| 28 days | 65 | 42 | 52 | 55 |
| Yellowing in the dark, 100 μm wet | | | | |
| b* Initial | 2.35 | 2.27 | 2.08 | 2.42 |
| db* after 14 days 50° C. | 1.29 | 0.96 | 1.04 | 1.17 |
| db* after 21 days 50° C. | 1.51 | 1.25 | 1.27 | 1.31 |

The results show that the paint (Example 8) formulated with a resin of the invention (Example 2b prepared from DMHHPA monomer (hydrogenated adduct of myrcene and citraconic anhydride) according to the invention—Example 2a) shows better hardness development results in comparison with prior art Paints D1 and E1 respectively formulated from comparative resins Comp D and E. Whereas all hydrogenated monomers (HHPA, MHHPA and DMHHPA) result in less yellowing paints compared to Paint A2 prepared using a resin (Comp A) made from a PA monomer, it is particularly surprising that Example 8 also has better hardness properties than Paints D1 and E1 formulated from resins prepared from monomers of respectively HHPA (Comp D) and MHHPA (Comp E), which are maleic anhydride based analogues of DMHHPA.

Example 9

Paints

Paints were produced by mixing in a Cowless dissolver resin solution (44 grams solid resin), 28 grams of Tioxide TR 92 (pigment) and 0.30 grams of Nuosperse FA 601 (dispersant) and milling them into a mill paste. To this paste were added under stirring 0.31 grams Borchi-Oxy-Coat (iron drier), 0.70 grams Calcium naphthenate (calcium drier), 1.83 grams Octasoligen Zirconium 12 (zirconium drier), 0.3 grams Borchinox M2 (antiskinning agent) and xylene to give application viscosity.

These paints showed the following properties (table 4).

| Paint | Paint A3 | Ex 9 | Paint G1 | Paint H1 | Paint J1 |
|---|---|---|---|---|---|
| Example resin used in paint | Comp A | Ex 3b | Comp G | Comp H | Comp J |
| Resin based on: | PA | CA-Myrcene | MA-Myrcene | CA-Rosin | CA-Rosin |
| Cotton wool drying, 100 μm wet | | | | | |
| dust free time (hr:min) | 0:19 | 2:30 | 1:38 | 3:00 | 2:30 |
| tack free time (hr:min) | 4:57 | 6:24 | 4:49 | >8:00 | 5:30 |
| König Hardness in sec, 100 μm wet | | | | | |
| 1 day | 33 | 20 | 19 | 39 | 13 |
| 7 days | 49 | 56 | 52 | 88 | 11 |
| 14 days | 63 | 91 | 94 | 115 | 14 |
| 28 days | 65 | 109 | 112 | 124 | 17 |
| Yellowing in the dark, | | | | | |

-continued

| Paint | Paint A3 | Ex 9 | Paint G1 | Paint H1 | Paint J1 |
|---|---|---|---|---|---|
| 100 μm wet | | | | | |
| b* Initial | 2.35 | 2.59 | 2.65 | 5.31 | 3.78 |
| db* after 14 days 50° C. | 1.29 | 2.25 | 2.70 | 4.40 | 4.71 |
| db* after 21 days 50° C. | 1.51 | 2.56 | 3.27 | 5.68 | 6.87 |

The results show that the paint (Example 9) formulated with a resin of the invention (Example 3b prepared from a citraconic anhydride—Myrcene adduct of the invention Example 3a) shows comparable hardness development and much better yellowing results in comparison with prior art Paint G1 formulated from comparative resin Comp G. The paint of the invention also shows (at equal or better hardness) much better yellowing results in comparison with prior art paints H1 and J1 formulated from prior art resins Comp H and Comp J based on patent publication WO2013/167662. Furthermore example 9 is a better paint than Paint A3 prepared using a resin (Comp A) made from a phtalic anhydride PA monomer, having much better hardness development.

Examples 10-12

Paints

Paints were produced by mixing in a Cowless dissolver resin solution (44 grams solid resin), 28 grams of Tioxide TR 92 (pigment) and 0.30 grams of Nuosperse FA 601 (dispersant) and milling them into a mill paste. To this paste were added under stirring 0.31 grams Borchi-Oxy-Coat (iron drier), 0.3 grams Exkin 2 (antiskinning agent) and xylene to give application viscosity.

These paints showed the following properties (table 5).

| Paint | Paint A4 | Ex 10 | Ex 11 | Ex 12 |
|---|---|---|---|---|
| Resin from example: | Comp A | 4a | 5a | 6a |
| Drying Dust free time (hrs:min) | 0:18 | 1:04 | 1:05 | 3:33 |
| Drying Tack free time (hrs:min) | 5:23 | 8:00 | 7:05 | 7:33 |
| König Hardness 1 day | 27 | 10 | 23 | 14 |
| König Hardness 7 days | 54 | 56 | 53 | 48 |
| König Hardness 14 days | 65 | 69 | 62 | 76 |
| König Hardness 28 days | 73 | 86 | 66 | 102 |
| Yellowing in the dark, 150 μm wet | | | | |
| b* Initial | 2.38 | 2.27 | 2.08 | 2.67 |
| Δb* after 14 days 50° C. | 1.13 | 0.75 | 0.95 | 2.64 |
| Δb* after 21 days 50° C. | 1.50 | 1.04 | 1.28 | 3.24 |

The results in table 5 show that the paints formulated with resins of the invention (Examples 10 to 12) show either better final hardness or better yellowing results (or both) in comparison with prior art Paint A4 formulated from comparative resin Comp A, just as was found above for Examples 8 and 9 respectively.

Examples 13-14

Emulsion Paints

A paste was produced by mixing in a Cowless dissolver 5.5 grams of demi water, 24 grams of Tioxide TR 92 (pigment), 1.2 grams of Disperbyk 2015 (dispersant), 1 gram of Rheolate 212 (thickener) and 0.2 grams of Byk 028 (antifoam agent) and milling them into a mill paste. To this paste were added under stirring resin emulsion (26.24 grams solid resin), 1.84 grams Borchi-Oxy-Coat 1101 diluted 9:1 in demi water (iron drier), 2.7 grams of Rheolate 644 (thickener) and demi water to give 100 grams of paint These emulsion paints showed the following properties (table 6).

| Paint | Paint K1 | Ex 13 | Ex 14 |
|---|---|---|---|
| Resin from example: | Comp K | 5b | 6b |
| Drying Dust free time (hrs:min) | 0:30 | 2:00 | 3:30 |
| Drying Tack free time (hrs:min) | 4:00 | 7:00 | 7:30 |
| König Hardness 1 day | 23 | 10 | 10 |
| König Hardness 7 days | 29 | 13 | 26 |
| König Hardness 14 days | 33 | 16 | 42 |
| König Hardness 28 days | 36 | 13 | 55 |
| Yellowing in the dark, 150 μm wet | | | |
| b* Initial | 2.34 | 2.24 | 2.80 |
| Δb* after 14 days 50° C. | 2.35 | 1.87 | 3.56 |
| Δb* after 21 days 50° C. | 3.09 | 2.42 | 4.29 |
| Water resistance average value (1-5) | 4.6 | 2.8 | 3.0 |
| Gloss, 100 μm wet after 1 day, 20°/60° | 89/96 | 70/87 | 89/97 |

The results in table 6 show that the paints formulated with emulsions of the invention (Examples 13 and 14) show either better final hardness or yellowing results in comparison with an optimized commercially available prior art based paint.

The invention claimed is:

1. An alkyd resin comprising the condensation product of at least the following components:
   (A) a polybasic acid,
   (B) a polyhydric alcohol, and
   (C) a linear C12-C60 hydrocarbo monocarboxylic acid, and optionally
   (D) at least one component other than the components (A) to (C), wherein
   at least a part of the polybasic acid (A) is a Diels Alder adduct of citraconic acid or citraconic anhydride with a C4-C14 conjugated diene, a half ester of the Diels Alder adduct and/or a diester of the Diels Alder adduct, and wherein
   the alkyd resin is free of rosin.

2. The alkyd resin according to claim 1, wherein the Diels Alder adduct is hydrogenated.

3. The alkyd resin according to claim 1, wherein the Diels Alder adduct is present in the alkyd resin in an amount of at least 25 wt. %, relative to total weight of the polybasic acid present in the alkyd resin.

4. The alkyd resin according to claim 1, which comprises is from 10 to 50% by weight of component (A), from 10 to 40% by weight of component (B), and from 1 to 80% by weight of component (C), wherein components (A) to (C) and optionally component (D) are present in a total amount of 100 wt. %.

5. The alkyd resin as claimed in claim 1, wherein component (C) is a fatty acid or a mixture of fatty acids.

6. The alkyd resin as claimed in claim 5, wherein the fatty acid comprises at least one double bond.

7. The alkyd resin as claimed in claim 5, wherein the fatty acids are obtained from natural sources selected from the group consisting of soyabean fatty acids, sunflower fatty acids, tall oil fatty acids, and linseed oil fatty acids.

8. The alkyd resin as claimed in claim 1, wherein component (B) is a polyalcohol with at least three hydroxyl groups selected from the group consisting of glycerol, trimethylolpropane, pentaerythritol, mannitol, sorbitol, sorbitan and mixtures thereof.

9. The alkyd resin as claimed in claim 1, wherein the component (A) comprises a polybasic acid selected from the group consisting of phthalic acid, maleic acid, fumaric acid, azelaic acid, succinic acid, itaconic acid, adipic acid, sebacic acid, furandicarboxylic acid, trimellitic acid, pyromellitic acid and mixtures thereof.

10. The alkyd resin as claimed in claim 1, wherein the C4-C14 conjugated diene is a conjugated diene that does not contain carboxylic acid functionality is selected from the group consisting of 1,3-butadiene, isoprene, terpenes containing conjugated double bonds and mixtures thereof.

11. The alkyd resin as claimed in claim 10, wherein the C4-C14 conjugated diene is myrcene and/or phellandrene.

12. The alkyd resin as claimed in claim 1, wherein the C4-C14 conjugated diene is isoprene, myrcene and/or limonene, and wherein the diene is treated with isomerization catalyst.

13. The alkyd resin as claimed in claim 1, wherein component (A) comprises a phthalic acid monomer in an amount which is lower than 25 wt. % relative to total weight amount of alkyd resin.

14. The alkyd resin as claimed in claim 1, wherein component (A) comprises an amount lower than 15 wt. %, relative to total weight of the alkyd resin, of a Diels Alder adduct of a conjugated diene and maleic acid and a Diels Alder adduct of a conjugated diene and maleic acid anhydride.

15. The alkyd resin as claimed in claim 1, wherein the alkyd resin is solvent borne or a solid.

16. A water borne alkyd emulsion comprising the alkyd resin as claimed in claim 1 and optionally at least one surfactant added either during or after the reaction of Components (A) to (D).

17. A process for preparing the alkyd resin as claimed in claim 1 comprising the steps of:
(a) preparing the Diels Alder adduct;
(b) optionally hydrogenating the Diels Alder adduct; and
(c) reacting the Diels Alder adduct obtained in step (a) or the hydrogenated Diels Alder adduct obtained in step (b) directly after preparation or alternatively after collection and isolation in an esterification step with an alkyd prepolymer to form the alkyd resin.

18. A process for preparing the alkyd resin as claimed in claim 1, wherein the process comprises the steps of:
(a) preparing the Diels Alder adduct;
(b) optionally hydrogenating the Diels Alder adduct; and
(c) reacting, in a (trans)esterification step, the Diels Alder adduct obtained in step (a) or the hydrogenated Diels Alder adduct obtained in step (b) directly after preparation or alternatively after collection and isolation with components (B), (C) and (D) and optionally with and additional polybasic acid of component (A) to form the alkyd resin.

19. A coating composition comprising the alkyd resin as claimed in claim 1.

20. A substrate or article having coated thereon the coating composition as claimed in claim 19.

21. A method for preparing a coated substrate or article comprising the steps of:
(i) applying the coating composition as claimed in claim 19 onto a substrate or article;
(ii) optionally drying the composition in situ; and/or
(iii) optionally curing the composition in situ.

* * * * *